United States Patent
Lee et al.

(10) Patent No.: US 12,292,385 B2
(45) Date of Patent: May 6, 2025

(54) GEMSTONE COLOUR GRADING PROCESS AND GRADING SYSTEM

(71) Applicant: GOLDWAY TECHNOLOGY LIMITED, Hong Kong (CN)

(72) Inventors: Wing Yan Lee, Hong Kong (CN); Juan Cheng, Hong Kong (CN); Chun Yan Dominique Lau, Hong Kong (CN); Wing Chi Tang, Hong Kong (CN); Ka Wing Cheng, Hong Kong (CN); Ching Tom Kong, Hong Kong (CN); Koon Chung Hui, Hong Kong (CN)

(73) Assignee: GOLDWAY TECHNOLOGY LIMITED, Hong Kong (CN)

( * ) Notice: Subject to any disclaimer, the term of this patent is extended or adjusted under 35 U.S.C. 154(b) by 520 days.

(21) Appl. No.: 17/312,240

(22) PCT Filed: Dec. 10, 2019

(86) PCT No.: PCT/CN2019/124269
§ 371 (c)(1),
(2) Date: Jun. 9, 2021

(87) PCT Pub. No.: WO2020/119673
PCT Pub. Date: Jun. 18, 2020

(65) Prior Publication Data
US 2022/0026371 A1    Jan. 27, 2022

(30) Foreign Application Priority Data
Dec. 10, 2018  (HK) .................................. 18115828.6

(51) Int. Cl.
*G01N 21/87* (2006.01)
*G01J 3/42* (2006.01)
(Continued)

(52) U.S. Cl.
CPC ................ *G01N 21/87* (2013.01); *G01J 3/42* (2013.01); *G01N 21/3103* (2013.01);
(Continued)

(58) Field of Classification Search
CPC ........... G01J 3/42; G01R 33/60; G01N 24/10; G01N 33/381; G01N 21/3103; G01N 21/87
See application file for complete search history.

(56) References Cited

U.S. PATENT DOCUMENTS

2017/0010217 A1    1/2017  Paleari

FOREIGN PATENT DOCUMENTS

| CA | 2937696 A1 | 9/2015 |
| CN | 1833164 A | 9/2006 |

(Continued)

OTHER PUBLICATIONS

D.J. Twitchen, "Correlation between ND1 optical absorption and the concentration of negative vacancies determined by electron paramagnetic resonance (EPR)", 1999 (Year: 1999).*

(Continued)

*Primary Examiner* — Maurice C Smith
(74) *Attorney, Agent, or Firm* — JCIP; Joseph G. Chu

(57) ABSTRACT

A process of assigning a colour grade to a diamond, including the steps of (i) determining the N3 and C-center content of a diamond (110); (ii) comparing the N3 and C-center content of the diamond with a previously acquired data set from a plurality of diamonds each having a colour grading previously assigned thereto, and (iii) assigning a colour grade to the diamond upon a correlation of the N3 and C-center content of said diamond with a grade of said previously acquired data set; wherein said previously acquired data set comprises a correlation between N3 and C center content and optical absorbance in the visible light spectrum for each diamond of said plurality of diamonds.

8 Claims, 13 Drawing Sheets

(51) Int. Cl.
   *G01N 21/31*   (2006.01)
   *G01N 24/10*   (2006.01)
   *G01N 33/00*   (2006.01)
   *G01R 33/60*   (2006.01)

(52) U.S. Cl.
   CPC ........... *G01N 24/10* (2013.01); *G01N 33/389* (2024.05); *G01R 33/60* (2013.01)

(56) References Cited

FOREIGN PATENT DOCUMENTS

| | | |
|---|---|---|
| CN | 101539530 A | 9/2009 |
| CN | 103090973 A | 5/2013 |
| CN | 104198456 A | 12/2014 |
| CN | 108027328 A | 5/2018 |
| CN | 108896546 A | 11/2018 |
| EP | 3376211 A1 | 9/2018 |
| RU | 2215285 C1 | 10/2003 |

OTHER PUBLICATIONS

D. A. Redman, "Spin Dynamics and Electronic States of N-V Centers in Diamond by EPR and Four-Wave-Mixing Spectroscopy", 1991 (Year: 1991).*

Examination Report dated Mar. 8, 2022 for Indian Application No. 202117029214.

Extended European Search Report with date of completion of Jun. 24, 2022 for European Application No. 19896882.8.

Zhiguo Ren et al: "Diamond color grading based on machine vision", 2009 IEEE 12th International Conference on Computer Vision Workshops, ICCV Workshops: Kyoto, Japan, Sep. 27-Oct. 4, 2009, Institute of Electrical and Electronics Engineers, Piscataway, NJ, Sep. 27, 2009 (Sep. 27, 2009), pp. 1970-1976, XP031664553, ISBN: 978-1-4244-4442-7, p. 1971; figure 1, p. 1974.

Titkov S V et al: "The luminescent nature of orange coloration in natural diamonds: optical and EPR study", Physics and Chemistry of Minerals, Springer, Berlin, DE, vol. 42, No. 2, Oct. 1, 2014 (Oct. 1, 2014), pp. 131-141, XP035437816, ISSN: 0342-1791, DOI: 10.1007/S00269-014-0705-x [retrieved on Oct. 1, 2014] p. 134 pp. 137-138.

Takahashi H et al: "Diamond color measurement instrument based on image processing", Proceeding of SPIE; [Proceedings of SPIE ISSN 0277-786X vol. 10524], SPIE, US, vol. 9970, Sep. 14, 2016 (Sep. 14, 2016), pp. 997015-997015, XP060079528, DOI: 10.1117/12.2235801 ISBN: 978-1-5106-1533-5 table 1.

International Search Report and Written Opinion of International Searching Authority for International Application No. PCT/CN2019/124269.

Search Report by Chinese Patent Office for Hong Kong Application No. 18115828.6.

Hearing Notice of Intellectual Property India dated Dec. 13, 2023 for Indian Application No. 202117029214.

First Office Action Dated Jan. 22, 2024 for Chinese Application No. 201980089350.0.

* cited by examiner

Grade D – M FTIR spectra

Grade D-M diamonds UV-Vis spectra

P1 center as indicated by arrows and P2 center is shown in the range 3400-3440 Gauss.

EPR spectrum of E, H and L grade diamonds.

EPR spectrum focused on where P2 and P1 center is located.

EPR spectrum of E and L grade diamond showing the difference in signal intensity Range selection for P2 + P1 center spin counting.

N3+ C- center EPR intensity of each color grade

UV-Vis N3+C-center absorbance concentration of each color grade diamond

Correlation between N3 + C-center intensity obtained in UV-Vis and EPR (Background Information)

GEMSTONE COLOUR GRADING PROCESS AND GRADING SYSTEM

TECHNICAL FIELD

The present invention relates to a system and a process for ascertaining colour of a gemstone. More particularly, the present invention provides a system and a process for ascertaining colour of a diamond.

BACKGROUND OF THE INVENTION

Diamonds are a key component utilized in luxury goods, in particular in articles of jewellery, and can have a very great value. The value of a diamond depends on several physical properties of the diamond.

There are four globally accepted standards utilized to assess the quality of a diamond, which are typically known as the 4C's, these being Clarity, Colour, Cut and Carat Weight.

For a diamond, with the exception colour of a diamond which may in some cases have a particular or fancy colour, the value of a diamond is highly dependent on what is known as its colourlessness. The more colourless the diamond, the higher or better the grade.

By way of example, the Gemological Institute of America (GIA) has a colour grade system from D to Z, for which the D grade denotes a diamond which is completely colourless, and ranging to a Z grade which denotes a diamond having a significant amount of unwanted colour.

Shown in FIG. 15 is the Gemological Institute of America (GIA) colour scale, against which a colour grading is applied, with the grades shown from colourless to light.

Although the human visual recognition of a different diamond colour may not necessarily be particularly sensitive in particular in relation to diamonds of similar grades, only a slightly change in colour can significantly affect the value of a diamond.

Several factors contribute to the colour of a diamond, the most common and important factor being impurities located within a diamond. During the formation process of diamonds, impurities are easily incorporated and are inherently present.

Nitrogen is the most common impurity found in natural diamonds, which produces an unwanted yellow colour. The higher nitrogen content in a diamond, the deeper colour and hence lower colour grade the stone is. The presence of boron within a diamond can also affect diamond colour of a diamond, but is less common. Diamonds with boron impurity show light blue colour. There are other impurities also affect diamond colour, however these are rare.

Apart from impurities, vacancy defects within a diamond also contribute to colour of a diamond. There are different forms of vacancies, such as isolated vacancy, multivacancy complex, and vacancy combining with impurities, for example.

In some diamonds, due to the ambient pressure conditions during the formation process deep in the earth when the diamond is formed, the carbon atoms may not form ideal tetrahedral structures, and the tetrahedral structures may be deformed. Such crystal deformation remaining in natural diamond can also cause colour changes.

As is known, for the assessment on the colour of a diamond, the most accepted industry standard and practice to determine a diamond's colour is by use of trained human eyes against standardized diamonds of standardized colour.

Using GIA as an example, colour grading personnel are trained for several months utilising standard master stones from a master stone set with assorted colour grades. Moreover, during the colour grading process by a diamond grader, a diamond under assessment is compared with the master stones side by side in a controlled environment.

The controlled environment is a standard light box with a white tile to place behind the master stones and testing diamond for which colour is being assessed as a backdrop. Under this standardized environment, the colour of a diamond can be graded by referring it to the master stone with the nearest colour by a grader.

A diamond, in accordance with the GIA colour assessment standard, as well as for other standards, is typically viewed from below the diamond at about 45 degrees to the pavilion, with a colour grader looking primarily at the pavilion and in a direction of towards the table of the diamond from the pavilion side.

Repetitive training of colour graders is applied and required, with a view so that different graders can reproduce the same assessment results, with a view to providing uniformity and consistency between colour grading personnel.

Although such a colour grading process is extensively used and under strict colour grading procedures, the reliability and repeatability of the colour grading methodology is still prone to inconsistencies, and such inconsistencies can cause incorrect grading of a diamond, which can adversely impact upon the correct value of a diamond.

OBJECT OF THE INVENTION

It is an object of the present invention to provide a system and a process for ascertaining or grading colour of a gemstone, in particular a diamond, which overcomes or at least partly ameliorates at least some deficiencies as associated with the prior art.

SUMMARY OF THE INVENTION

In a first aspect, the present invention provides a process of assigning a colour grade to a diamond, said process including the steps of:
(i) determining the N3 and C-center content of a diamond;
(ii) comparing the N3 and C-center content of said diamond with a previously acquired data set from a plurality of diamonds each having a colour grading previously assigned thereto, and
(iii) assigning a colour grade to the diamond upon a correlation of the N3 and C-center content of said diamond with a grade of said previously acquired data set;
  wherein said previously acquired data set comprises a correlation between N3 and C center content and optical absorbance in the visible light spectrum for each diamond of said plurality of diamonds.

Preferably, the N3 and C-center content of the diamond is determined by Electron paramagnetic resonance (EPR). Preferably, said optical absorbance is N3 and C-center absorbance in the Ultraviolet Visible (UV-Vis) spectrum. The N3 and C-center absorbance is preferably determined by way of a UV-Vis-NIR Spectrometer.

Preferably the colour grading previously assigned to each diamond of said plurality of diamonds is the Gemological Institute of America (GIA) colour grading.

In a second aspect, the present invention provides a process of assigning a colour grade to a diamond, said process including the steps of:
(i) determining the optical absorbance in the visible light spectrum of a diamond;
(ii) comparing the optical absorbance of said diamond with previously acquired data set from a plurality of diamonds each having a colour grading previously assigned thereto, and
(iii) assigning a colour grade to the diamond upon a correlation of the optical absorbance of said diamond with a grade of said previously acquired data set;
wherein said previously acquired data set comprises a correlation between N3 and C center content and optical absorbance in the visible light spectrum for each diamond of said plurality of diamonds.

Preferably, the N3 and C-center content of the diamond is determined by Electron paramagnetic resonance (EPR).

Preferably, said optical absorbance is N3 and C-center absorbance in the Ultraviolet Visible (UV-Vis) spectrum. Preferably said N3 and C-center absorbance is determined by way of a UV-Vis-NIR Spectrometer.

The colour grading previously assigned to each diamond of said plurality of diamonds is preferably the Gemological Institute of America (GIA) colour grading.

In a third aspect, the present invention provides a process operable using a computerized system for grading the colour of a diamond, the computerized system including a processor module and an output module operably interconnected together, said process including the steps of:
(i) acquiring data indicative of the N3 and C center content of a diamond from an Electron Paramagnetic Resonance (EPR) device;
(ii) in a processor module comparing data derived from the Electron Paramagnetic Resonance (EPR) device, with a plurality of data sets each of which corresponds to a diamond of a plurality of diamonds, wherein said data sets are previously acquired data comprises a correlation between N3 and C center content and optical absorbance in the visible light spectrum for each diamond of said plurality of diamonds; and
(iii) from an output module, responsive to a predetermined threshold of correlation between the data derived from input of the Electron Paramagnetic Resonance (EPR) device and one of the plurality of data sets from step (ii), an output signal is provided indicative of the colour grade of the diamond.

Preferably, said optical absorbance is N3 and C-center absorbance in the Ultraviolet Visible (UV-Vis) spectrum. Preferably, said N3 and C-center absorbance is determined by way of a UV-Vis-NIR Spectrometer.

The colour grading previously assigned to each diamond of said plurality of diamonds is preferably the Gemological Institute of America (GIA) colour grading.

In a fourth aspect, the present invention provides a process operable using a computerized system for grading the colour of a diamond, the computerized system including a processor module and an output module operably interconnected together, said process including the steps of:
(i) acquiring data indicative of the optical absorbance in the visible light spectrum of a diamond from a light absorbance device;
(ii) in a processor module comparing data derived from the light absorbance device, with a plurality of data sets each of which corresponds to a diamond of a plurality of diamonds, wherein said data sets are previously acquired data comprises a correlation between N3 and C center content and optical absorbance in the visible light spectrum for each diamond of said plurality of diamonds; and
(iii) from an output module, responsive to a predetermined threshold of correlation between the data derived from input of a light absorbance device and one of the plurality of data sets from step (ii), an output signal is provided indicative of the colour grade of the diamond.

Preferably, said optical absorbance is N3 and C-center absorbance in the Ultraviolet Visible (UV-Vis) spectrum. Preferably, said N3 and C-center absorbance is determined by way of a UV-Vis-NIR Spectrometer.

The colour grading previously assigned to each diamond of said plurality of diamonds is preferably the Gemological Institute of America (GIA) colour grading.

In a fifth aspect, the present invention provides a system for grading the colour of a diamond, said system comprising:
(i) an input module for receiving data acquired indicative of the N3 and C center content of a diamond from an Electron Paramagnetic Resonance (EPR) device;
(ii) a processor module for comparing data by the input module derived from the Electron Paramagnetic Resonance (EPR) device, with a plurality of data sets each of which corresponds to a diamond of a plurality of diamonds, wherein said data sets are previously acquired data comprises a correlation between N3 and C center content and optical absorbance in the visible light spectrum for each diamond of said plurality of diamonds; and
(iii) an output module, which responsive to a predetermined threshold of correlation between the data derived from input of the Electron Paramagnetic Resonance (EPR) device and one of the plurality of data sets from the processor module, provides an output signal indicative of the colour grade of the diamond.

Preferably, said optical absorbance is N3 and C-center absorbance in the Ultraviolet Visible (UV-Vis) spectrum. Preferably, said N3 and C-center absorbance is determined by way of a UV-Vis-NIR Spectrometer.

The colour grading previously assigned to each diamond of said plurality of diamonds is preferably the Gemological Institute of America (GIA) colour grading.

In a sixth aspect, the present invention provides a system for grading the colour of a diamond, said system comprising:
(i) an input module for receiving data acquired indicative of the optical absorbance in the visible light spectrum of a diamond from a light absorbance device;
(ii) a processor module for comparing data derived from the input module from the light absorbance device, with a plurality of data sets each of which corresponds to a diamond of a plurality of diamonds, wherein said data sets are previously acquired data comprises a correlation between N3 and C center content and optical absorbance in the visible light spectrum for each diamond of said plurality of diamonds; and
(iii) an output module, which responsive to a predetermined threshold of correlation between the data derived from input of the light absorbance device and one of the plurality of data sets, provides an output signal is provided indicative of the colour grade of the diamond.

Preferably said optical absorbance is N3 and C-center absorbance in the Ultraviolet Visible (UV-Vis) spectrum. Preferably said N3 and C-center absorbance is determined by way of a UV-Vis-NIR Spectrometer.

The colour grading previously assigned to each diamond of said plurality of diamonds is preferably the Gemological Institute of America (GIA) colour grading.

BRIEF DESCRIPTION OF THE DRAWINGS

In order that a more precise understanding of the above-recited invention can be obtained, a more particular description of the invention briefly described above will be described by reference to specific embodiments thereof that are illustrated in the appended drawings. The drawings presented herein may not be drawn to scale and any reference to dimensions in the drawings or the following description is specific to the embodiments disclosed.

DETAILED DESCRIPTION OF THE DRAWINGS

Figure 1:
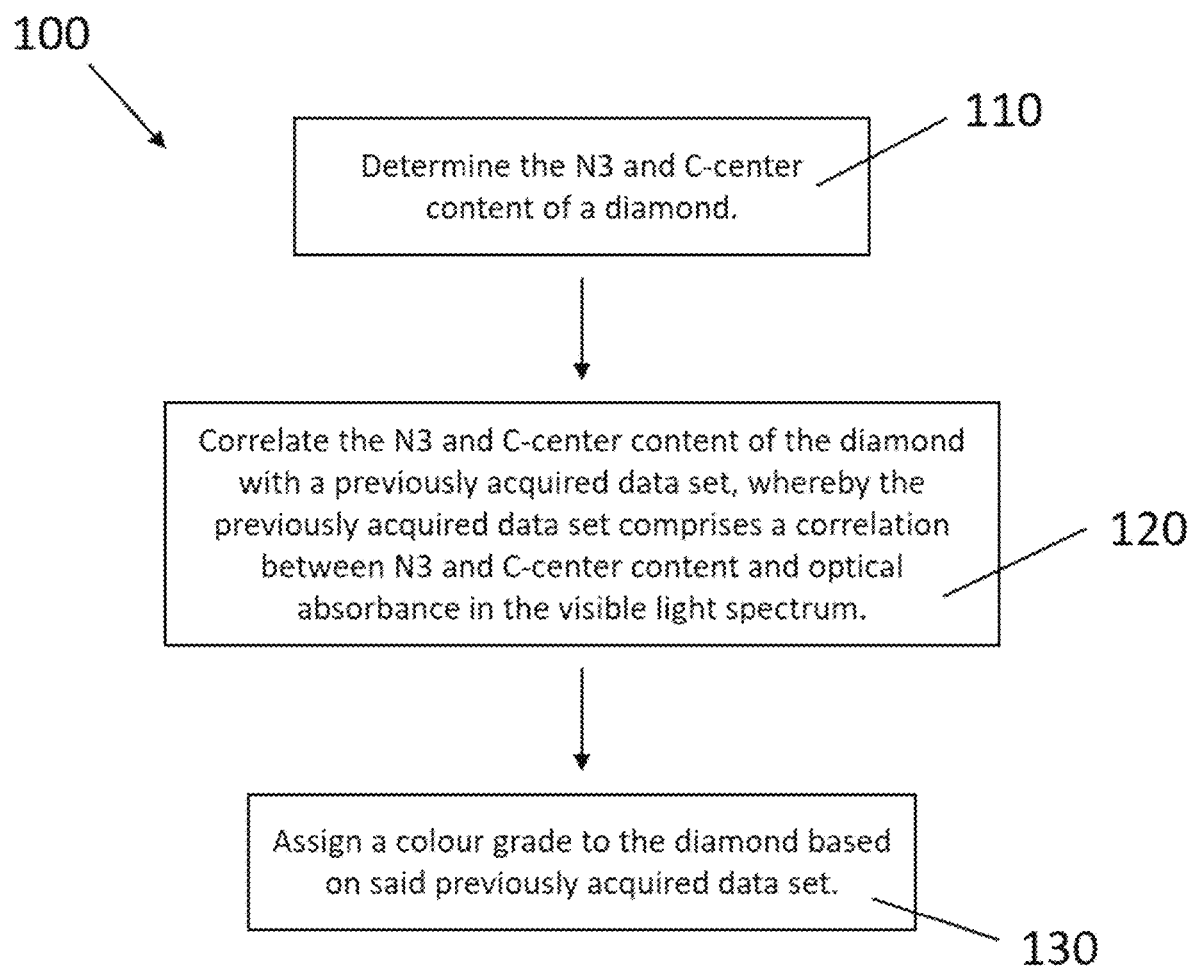
FIG. 1 shows a flow chart of a first embodiment of a process of the present invention.

The present inventors have identified shortcomings in the manner in which colour grading of diamonds is performed, and upon identification of the problems with the prior art, have provided a system and process which overcomes the problems of the prior art, and provides a system and process which is more consistent and reliable.

1. PROBLEMS IDENTIFIED BY THE PRESENT INVENTORS

Problems identified by the present inventors include as follows:

1.1 Intrinsic Factors-Reference Master Stones

For the standard reference of colour grades, the master stones are required to be with very high accuracy and repeatability amongst different sets.

As it is very difficult to select master stones from natural diamonds in large amounts matching the standard colours and other physical requirements, the master stones can be real or synthetic diamonds, zirconia or other appropriate materials. Regardless of the material which the master stones are formed from, they must be of the same size and of the same cut within the same set for consistency.

However, as diamonds requiring grading inherently have different sizes other than those of a master set, in order for an appropriate comparison to be made by a grader, a master stone set with similar sizes to the diamond should be used so as to reduce optical comparison error.

Inherently, it is very expensive and commercially impractical to have sets of master stones covering a range so as to cover all sizes of diamonds for assessment.

Further and more importantly, each master stone must be homogenously saturated with the specific standard colour in order that a best comparison may be made between a stone to be graded and the reference stone by the colour grader.

The accuracy and usability of master stones are not only applicable to different sets of master stones, but also the same sets of master stones at different points in time when assessment is made.

As such, the colour of the master stones of the standard set must be permanent without any changes over time, otherwise it is necessary to provide useable lifetimes to the master stones. After the expiration of the usable or serviceable lifespan of a master stone, there is no guarantee that the colour of the stone will remain stable, and consequently no guarantee as to the accuracy and repeatability of colour grading assessment.

All of the above-mentioned issues affect accuracy and repeatability, and give rise to high technical difficulties and hence high production cost of master stone sets for colour grading purposes.

1.2 Extrinsic Factors—Environmental Issues

Even with the most reliable master stones and within the guaranteed lifetime such that variance due to intrinsic factors is minimised, inherently the reliability and repeatability of the use human eyes and a person for colour grading, will still pose an issue to the correct colour grading of a diamond.

Colour perception is a common psychological effect on human colour vision. Any differences in the background colour and lighting condition, can contribute to errors in colour grading. As such, environmental parameters may also have an effect on colour grading consistency and accuracy.

1.3 Extrinsic Factors—Human Error Inconsistency and Perception

Due to the physiological effect of human's vision, tiredness and different judgements performed on the same diamond may also be made before and after assessments on many different stones, even by the same colour grader. As such, assessment of colour of the same diamond by the same person at different time may produce colour grade deviation.

Even with strictly controlled environment and a well-rested person, the physical properties of a diamond can also affect the colour grading. The cut of a diamond can introduce physical effect on colour judgement and assessment.

The very high refractive index of diamonds causes total internal reflection and dispersion of light, which can also affect accurate colour grading. The cut varies between different diamonds, so there are no corresponding master stones for every diamond for fair comparison.

Therefore, under standardized training and assessment procedures, professional colour graders still face difficulty for the reliability and repeatability because of the psychological, physiological, and physical effects.

1.4 Consumer View Factors

For the consumer's point of view, the pavilion, as commonly used for colour grading and assessment, is not the most obvious part of the diamond and not representative of the view of a diamond observed by a consumer.

For most articles of jewellery, diamonds are mounted with the tables facing out, which makes the pavilion facets not typically seen by people or minimally seen. Furthermore, pavilion facets are typically obscured by a setting such as claws, prongs and bezels.

As such, colour grading from the pavilion view as used in the prior art does not truly reflect the true perceptual colour seen by consumers.

1.5 Physical Factors

There exist other physical factors affecting diamond colour grading from the pavilion view of the prior art, leading to an insufficient colour grading process being provided.

One such factor is that the light directly from the white light source is reflected by the pavilion facets outside the diamond. This reflected light can affect the accuracy of colour grading, as the facets reflecting the light appear paler in colour.

Furthermore, when viewing pavilion facets of a diamond, multiple facets are typically seen which are at different angles to each other, causing different impressions of colour to the grader.

Apart from round brilliant cut diamonds, diamonds can also be cut in different fashions and cut-types, such as Princess, Oval, Marquise, Pear shaped, Cushion, Emerald, Asscher, Radiant and Heart shaped cuts and the like.

The light coming out from a pavilion at 45 degrees inherently is no longer representative in comparison with a master set having a different pavilion angle. As such, the colour of such other diamonds is to be graded at different directions.

2. SPECIFIC INVENTION BACKGROUND

White diamonds colour grading is one of the basic diamond evaluations and informs its colour value based on a scale that ranges from D to Z, the main industry accepted colour grading scale of GIA as discussed above, with D being the more colourless and more valuable, among other qualifications of diamonds.

As the diamond grade moves along the scale, its colour appears more yellow progressively. This yellowish colour, present only in Type I diamonds, is mainly due to the nitrogen content inside displayed as N3 center and C-center.

The current colour grading system by GIA, a discussed above, is based on a visual observational method, where gemologists compare the sample with a Master Stone (Colour) set. However, this method is very subjective.

The current colour grading method of GIA is based manually and visually by gemologist, where the diamond is viewed under a specific lighting against a white background and then compared to a master set of colour stones [1], further as discussed above.

Diamonds that belong to a higher colour grading present a colourless or near colourless appearance, while those that are of a more yellow in colour are classified as a lower colour grade. This change in colour is mainly due to the concentration of N3 and C-center in diamond [2-4]. The higher the concentration of both centers, the more yellow coloured the diamond will be [3].

However, this visual grading is a very subjective method, and its integrity is questioned as it is solely based on observation and judgement made by a human being, and an actual figure or quantification of N3 and C-center concentration, the main contributing factors influencing the human optical observable phenomena or impression of yellowishness, cannot be provided in such a process conducted by a human being.

There exist technical instruments that can be utilised in determining whether nitrogen is present in a diamond, including among others Fourier Transform Infrared Spectroscopy (FTIR), Raman Spectroscopy and UV-Vis Spectroscopy.

For an N3 center, it presents a distinguished peak at 415 nm which can be measured using Raman and UV-Vis spectroscopy, while a C-center presents an absorption continuum at a wavelength of 477 nm [4]. These optical-based instruments are able to detect such defects present in a diamond quite accurately.

However, as has been noted by the present inventors, it is difficult to provide an accurate quantification of such defects of a diamond, as a variety of factors can influence a reading and thus affect an outcome, such factors including the orientation of the sample and the area/volume covered during such a reading being acquired, for example.

Electron paramagnetic resonance (EPR), by contrast, is a magnetic resonance method that targets the measurement of unpaired electrons present in a sample [5, 6]. Thus, signals from other non-paramagnetic components present in a diamond will not be identified and thus not measured, which arguably provides a more accurate or complete reading.

N3 center and C-center are paramagnetic elements [7-9] that may possibly be measured utilised EPR, and its signal would appear on the spectrum within the range of from 3370 to 3460 Gauss.

A reading obtained from such methodology would then be required to be subjected to further processing under different parameters for its quantification method by spin counting. [10]

3. GENERAL INVENTION CONCEPT OF PRESENT INVENTION

The present inventors, having identified the shortcomings of colour grading of gemstones, in particular of diamonds, and more particularly white diamonds, have provided a process and system which overcomes the disadvantages of the prior art, including those as identified by the present inventors and as discussed above.

To overcome these repeatability and reliability difficulties, the present inventors have provided a system and process to reliably, repeatedly and consistently grade the colour of a diamond, which obviate the above intrinsic and extrinsic factors which affect the assessment when grading the colour of a diamond, as well as advantageously provides a system and process which overcomes consumer view factors and provides a more useful colour assessment and grading process than provided by the prior art.

In the present invention, the present inventors have considered all drawbacks with existing techniques for the grading of colour of diamonds, and have provided a system and process exhibiting superior consistency, repeatability, and which obviates the necessity of multiple master stone sets, as well as obviates the necessity of human judgement in the prior art and standardized lighting conditions assessment environments.

The present inventors have noted that as "colour" of a diamond, that being an optically assessable and discernable of the amount of yellowishness of diamond by the human eye, must be a benchmark-type characteristic in a colour assessment system or grading system.

As the value or appeal or a diamond is correlatable to colour, which is the amount of yellowishness, any scale or system must be compatible with such known and industry and market expectations, and as is known the "C" being "colour" is one of the four C's pertaining to value and/or appeal of a diamond.

Thus, whist it is conceivable that scientific colour rating or banding processes and systems could exist for quantifying colour associated parameters of a diamond, any colour grading system and process must be compatible with the key factor of colour associated with a diamond, this being the optical impression of the degree of yellowishness of the diamond.

Existing master stone sets are the benchmark for ascertaining the colour of a diamond, by specialist gemologists, and this optical impression must form the cornerstone of any diamond colour assessment system or scale, for relevance.

In accordance with the present invention, the present inventors have proposed a process and system which obviates human assessment and all the above associated inconsistencies and inconveniences, which is repeatable, which does not require the use of different master stone sets for assessment of diamonds of difference sizes, and which provides a grading which is compatible and which can be accorded to an established colour grading system, such as the GIA colour grading system.

3.1 Predefined Master Set

A set of master diamonds is utilised, of the same size (carat) which are considered to provide an optically appropriate segmentation or grading, as optically discerned, or the degree of "yellowness" of "yellowishness", whereby the set comprises appropriately distinguishable diamonds of a suitable degree of banding for optical grading and assessment.

3.2 Absorbance—Yellow Optical Impression

The diamonds of the master set are each analysed within an appropriate wavelength range, so as to determine the absorbance concentration, which provides the optical effect or impression of yellowishness, the cornerstone of colour grading.

Whilst the present inventors have noted there are numerous aspects of a diamond which may contribute in some manner to the optical impression of yellowness of a diamond by the human eye, such as impurities, includes, elements and the like, the present inventors have noted and considered that the N3 center and the C-center have the predominant effect of the optical impression of the presence of yellow of a diamond.

Accordingly, whilst the present invention in its broadest aspect accommodates for consideration of a variety of contributing aspects to the colour (yellowness) of a diamond by determining the absorption for example at room light and/or across a visible light spectrum, within the confines of the human perception of colour, the present inventors have found that determining the absorbance in the UV visible spectrum so as to determine absorbance for the N3 center (with its distinguished absorption peak at 415 nm) and the C-center (with an absorption continuum at 478 nm) whereby the blue colour band is absorbed, to be appropriate as such blue band absorption is what causes the overarching effect providing the optical phenomena of the presence of yellow and hence the colour of a diamond.

3.3 N3 Center and C-Center Quantification

Electron Paramagnetic Resonance (EPR) is used for a quantitative measurement of N3 center and C-center through spin counting, for each of the diamonds of the same master set.

3.4 UV Vis N3 Center and C-Center Absorbance and N3 Center and C-Center Quantification Grade Correlation Again although optical absorbance may within the scope of the invention be determined across the visible light spectrum of part thereof, as utilised in preferred embodiments, the UV Vis N3 center and C-center absorbance concentration is of each diamond of the master set, which his representative of a predetermined colour grade of 3.2 is correlated with the N3 center and C-center EPR intensity, for each diamond of the master set of the corresponding colour grade, so as to form a reference data set.

3.5 Grading of Unknown Diamond

In order to grade the colour of an unknown diamond, the N3 center and C-center EPR intensity, or the N3 center and C-center absorbance concentration (or optical absorption in the visible light spectrum in other embodiments), is determined for the unknown diamond, the reading of which is correlated with the reference data set as described at 3.4, and upon a suitable correlation being found, a grade is applied to the diamond of an unknown colour grade.

Accordingly, the present invention provides both a system and a process for the determination of the colour grade of a diamond.

4. Examples of Process and System of Present Invention

Referring FIG. 1, there is shown a flow chart of a first embodiment of a process 100 for assigning a colour grade to a diamond, according to the present invention.

The process 100 includes the steps of (i) determining the N3 and C-center content of a diamond (110); (ii) comparing the N3 and C-center content of said diamond with a previously acquired data set from a plurality of diamonds each having a colour grading previously assigned thereto (120) and (iii) assigning a colour grade to the diamond upon a correlation of the N3 and C-center content of said diamond with a grade of said previously acquired data set (130).

The previously acquired data set comprises a correlation between N3 and C center content and optical absorbance in the visible light spectrum, for each diamond of said plurality of diamonds.

The N3 and C-center content of the diamond is preferably determined by Electron paramagnetic resonance (EPR).

The optical absorbance is preferably N3 and C-center absorbance in the Ultraviolet Visible (UV-Vis) spectrum, and the N3 and C-center absorbance is determined by way of a UV-Vis-NIR Spectrometer.

The colour grading previously assigned to each diamond of said plurality of diamonds can be the Gemological Institute of America (GIA) colour grading. Alternatively, other new of existing colour grading systems may be implemented.

The process may be implemented in a computerized system.

Figure 2:
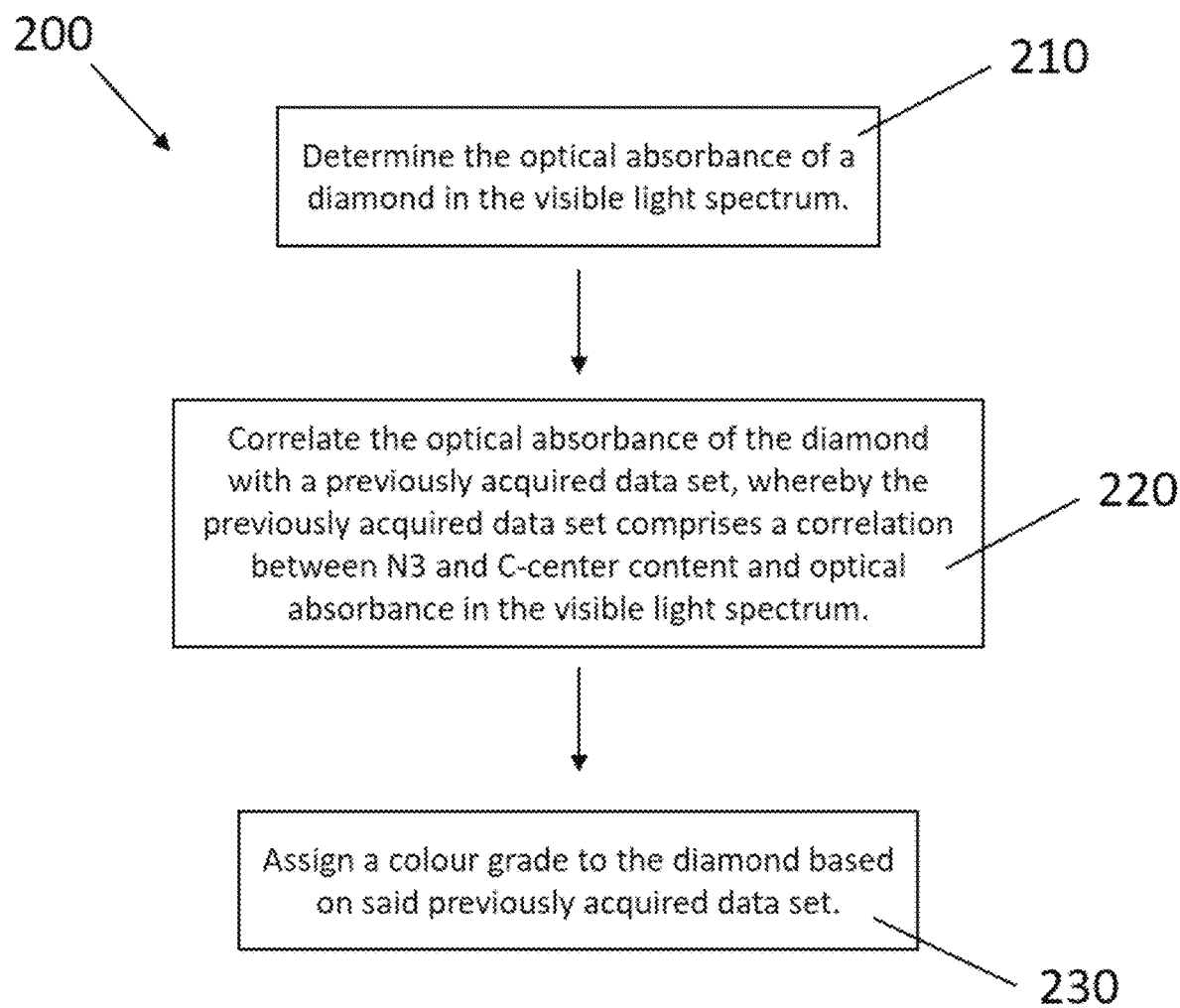
FIG. 2 shows a flow chart of a second embodiment of a process of the present invention.

Referring FIG. 2, there is shown a flow chart of a second embodiment of a process 200 for assigning a colour grade to a diamond, according to the present invention The process includes the steps of (i) determining the optical absorbance in the visible light spectrum of a diamond (210), (ii) comparing the optical absorbance of said diamond with a previously acquired data set from a plurality of diamonds each having a colour grading previously assigned thereto (220), and (iii) assigning a colour grade to the diamond upon a correlation of the optical absorbance of said diamond with a grade of said previously acquired data set (230).

The previously acquired data set comprises a correlation between N3 and C center content and optical absorbance in the visible light spectrum for each diamond of said plurality of diamonds.

Figure 3:
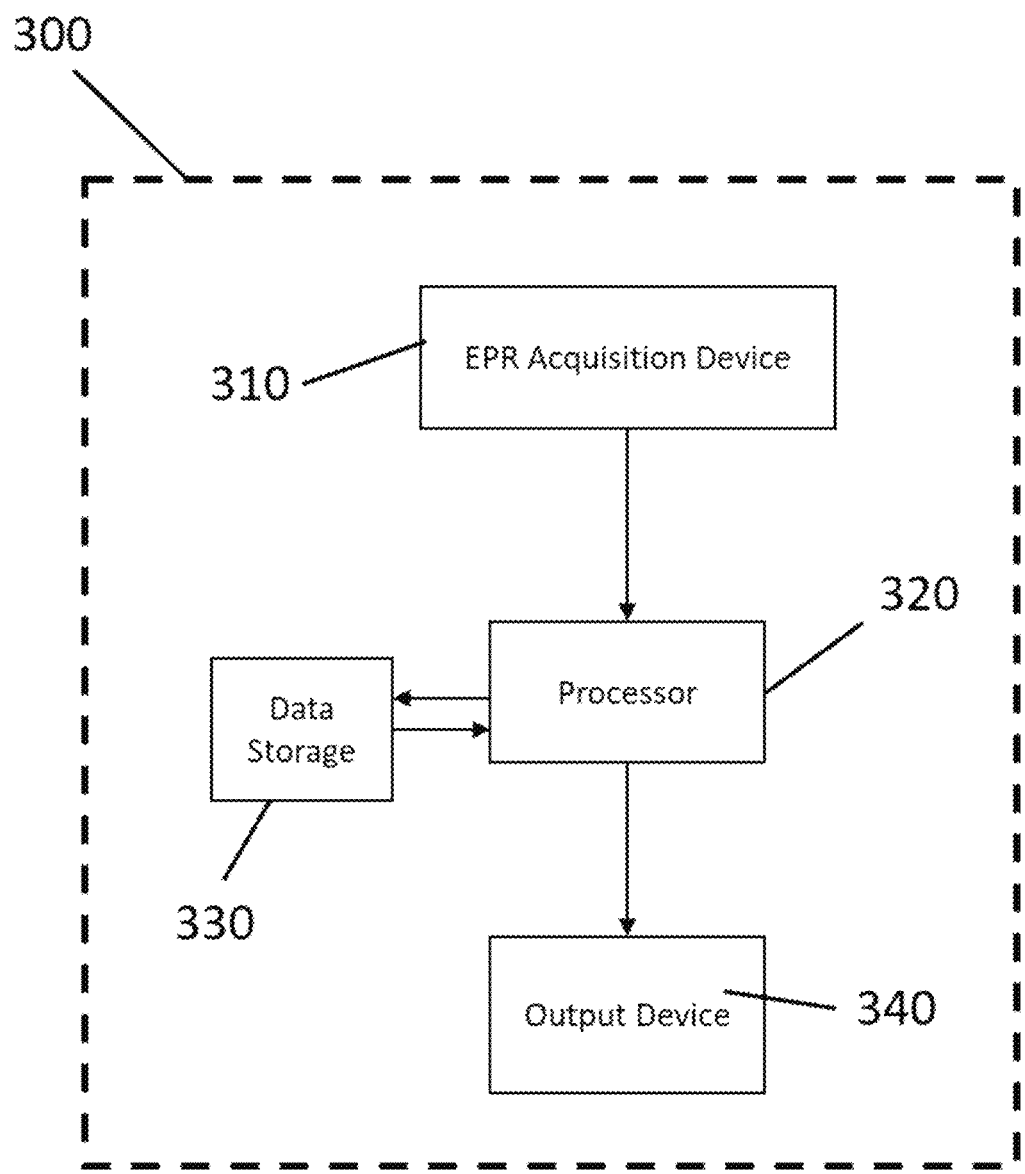
FIG. 3 shows a schematic representation of a first embodiment of a system according to the present invention.

FIG. 3 shows a schematic representation of a first embodiment of a system 300 according to the present invention.

The system 300 includes an EPR acquisition device 310 for acquiring N3 and C center content of a diamond from an Electron Paramagnetic Resonance (EPR) device; a processor 320 for comparing data derived from the Electron Paramagnetic Resonance (EPR) device 310, with a plurality of data sets each of which corresponds to a diamond of a plurality of diamonds stored in data store 330 and in communication with the processor 320, wherein the data sets are previously acquired data which comprises a correlation between N3 and C center content and optical absorbance in the visible light spectrum for each diamond of said plurality of diamonds; and an output device 330, which responsive to a predetermined threshold of correlation between the data derived from input of the Electron Paramagnetic Resonance (EPR) device 310 and one of the plurality of data sets from the processor module, provides an output signal indicative of the colour grade of the diamond.

Figure 4:
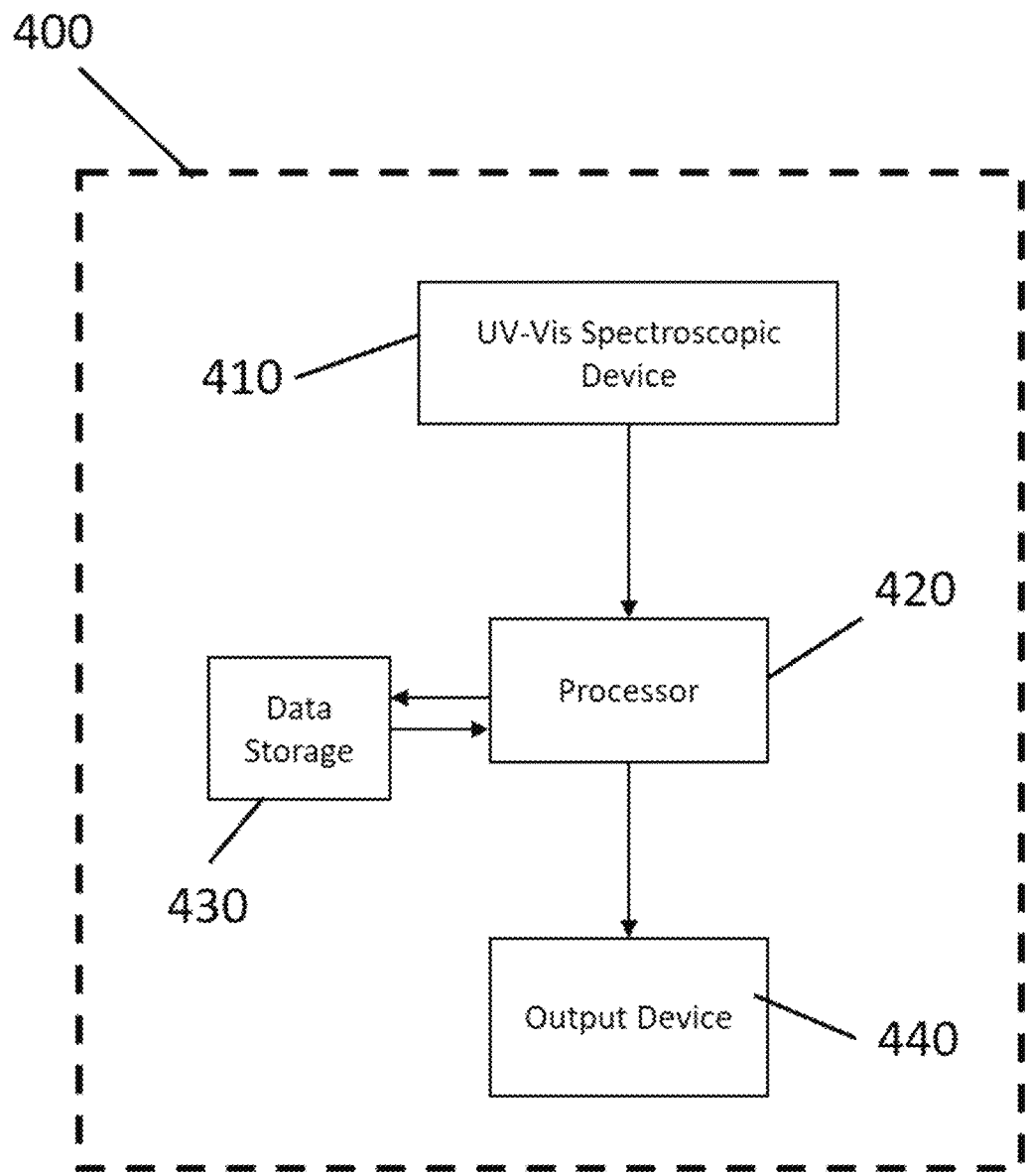
FIG. 4 shows a schematic representation of a second embodiment of a system according to the present invention.

FIG. 4 shows a schematic representation of a second embodiment of a system 400 according to the present invention.

A system 400 comprising a UV-Vis spectroscopic device 410 for acquiring data indicative of the optical absorbance in the visible light spectrum of a diamond from a light absorbance device; a processor 420 for comparing data derived from the input module from the UV-Vis spectroscopic device 410, with a plurality of data sets each of which corresponds to a diamond of a plurality of diamonds stored in data store 430 and in communication with the processor 420, wherein said data sets are previously acquired data comprising a correlation between N3 and C center content and optical absorbance in the visible light spectrum for each diamond of said plurality of diamonds; and an output device 440, which responsive to a predetermined threshold of correlation between the data derived from input of the light absorbance device and one of the plurality of data sets, provides an output signal is provided indicative of the colour grade of the diamond.

5. EXPERIMENTAL MODEL & DEMONSTRATION OF PRESENT INVENTION

In order to validate and demonstrate the applicability of the present invention, experimental analysis was conducted.

With the experimental evaluation, a master stone set was utilised, with diamonds ranging from a colour grade of D to M according to the existing GIA grade system, which were selected and assigned by a very experienced gemologist having a very long history and experience in gemstone grading.

5.1 FTIR Evaluation of Diamond Type for Master Set Diamonds

Figure 5:
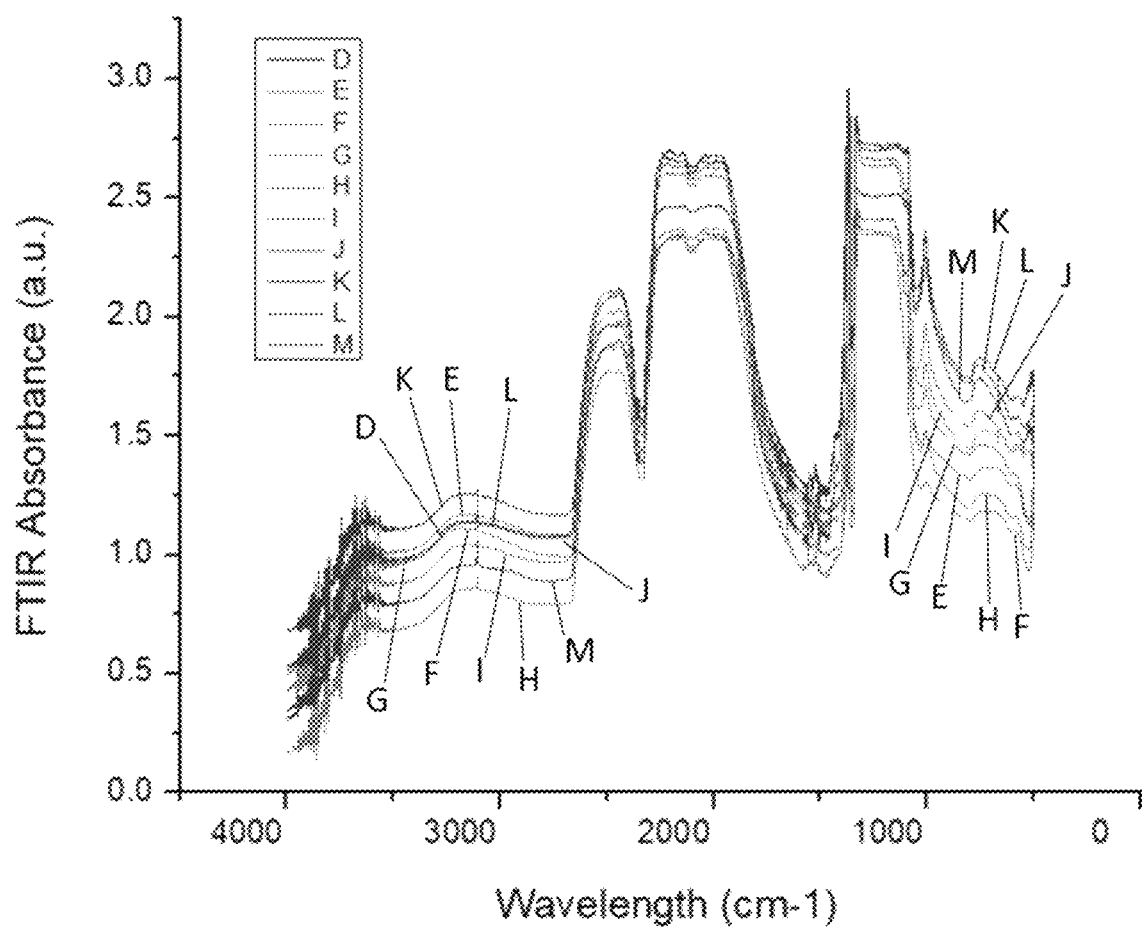
FIG. 5 shows an FTIR spectra of grade D to grade M of a master stone set of diamonds as used in the validation of the present invention.

The output of the FTIR absorbance versus wavelength for the diamonds of each grade is shown in FIG. 5.

The infrared absorption spectrum collected using FTIR of the master set of diamonds showed and demonstrated the diamonds of the set to be Type IaA and Type IaAB.

The samples information is summarized in the table below in Table 1.

TABLE 1

D to M grade diamonds with its respective weight and FTIR results.

| Diamond Grade | Weight (carat) | FTIR Results |
|---|---|---|
| D | 0.50 | Type IaA |
| E | 0.50 | Type IaAB |
| F | 0.50 | Type IaAB |
| G | 0.51 | Type IaAB |
| H | 0.50 | Type IaAB |
| I | 0.50 | Type IaAB |
| J | 0.50 | Type IaAB |
| K | 0.50 | Type IaAB |
| L | 0.50 | Type IaAB |
| M | 0.50 | Type IaAB |

5.2 UV-Vis Specta of Master Set Diamonds

Figure 6:
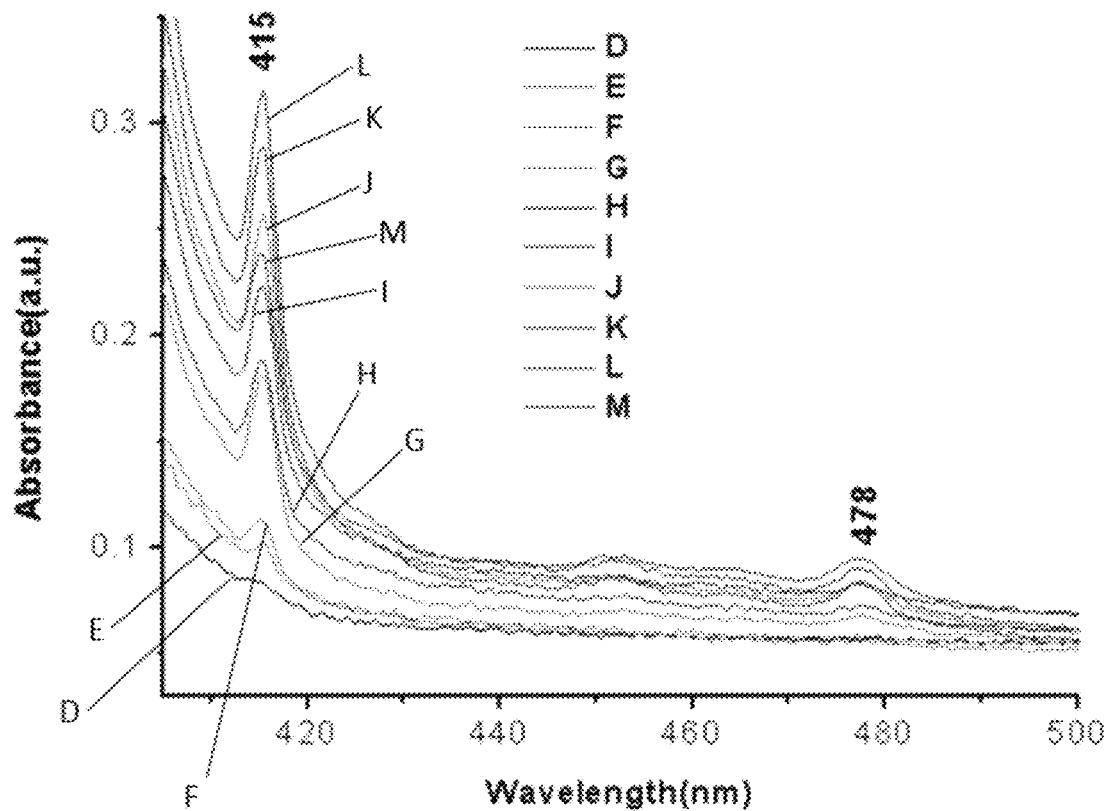
FIG. 6 shows a UV-Vis spectra of the grade D to grade M diamonds of the master set of FIG. 5, with the N3 and C-Center.

UV-Vis absorption spectra were collected for each diamond of the set of the master diamonds as shown in FIG. 6.

The measurements of UV-Vis were conducted using an Agilent Technologies Cary Series UV-Vis-NIR Spectrometer with Diffuse Reflectance Accessory and collected at room temperature. Wavelength range set from 200-800 nm.

As mentioned above, whilst other wavelength of spectra can be used in the broadest aspect of the invention, the present inventors have chosen to consider N3 and C-centre as the predominant contributors to the optically discernable parameter of colour, that is the human perception of yellowness or yellowishness of a diamond, and using UV-Vis has been considered to be appropriate for reasons as discussed above.

5.3 EPR Spectra

EPR spectrum of each of the diamonds of the master set was measured and collected with Bruker ELEXSYS-II system with a SHQE resonator.

All measurements were conducted under continuous wave (CW) and the conditions are summarized as follows in Table 2.

Each diamond sample of the master set was placed inside a quartz tube with a diameter of 10 mm during acquisition of the reading.

TABLE 2

| Measurement Parameters | EPR spectrum of diamond | EPR spectrum for Spin counting |
|---|---|---|
| Attenuation (dB) | 60 | 18.6 |
| Modulation Frequency | 100 | 100 |
| Modulation Amplitude | 1 Gauss | 2 Gauss |
| Points | 1024 | 1024 |
| Scan(s) | 1 & 20 (for high resolution) | 1 |
| Sweep Width | 200 Gauss | 50 Gauss |

EPR measurement parameters and conditions

Figure 7:
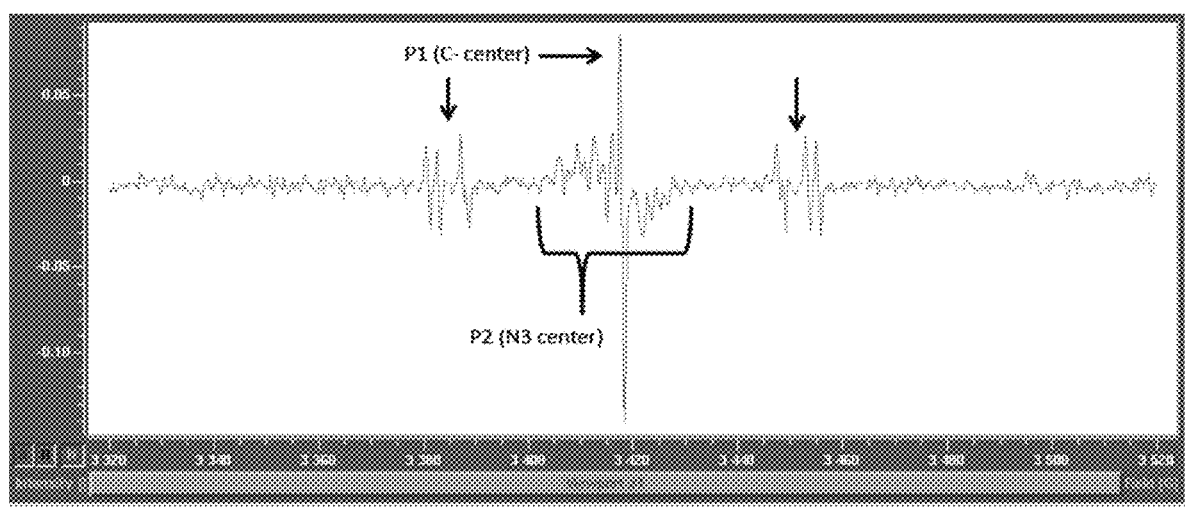
FIG. 7 shows an intensity spectrum with P1 and P2 Centers shown within the range of 3400-3440 Gauss.

N3 center and C-center are named P2 center and P1 center in EPR, respectively, and both centers can be detected and measured under continuous wave mode as demonstrated in FIG. 7.

5.4 Discussion of Experimental Evaluation and Model

The center peak and the satellite lines on both sides, as denoted by arrows in FIG. 3, corresponds to P1 center, while P2 center is displayed as one broad collection of lines in the range of 3400-3440 Gauss.

Figure 8:
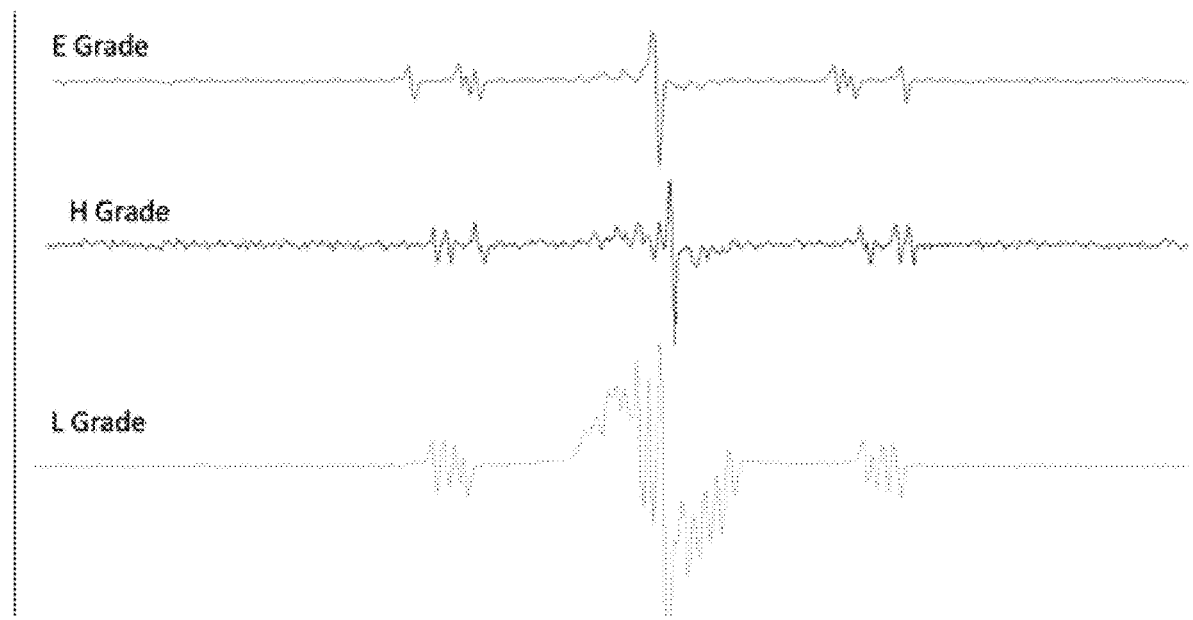
FIG. 8 shows an EPR spectrum of E, H and L grade diamonds of the master stone set.

A comparison of spectrum between diamonds of different colour grades diamonds is shown in FIG. 8.

As can be seen from the experimental results, the intensity of P2 center intensifies as it advances on the colour grade scale, whereby EPR spectrum of E, H and L grade diamonds is shown.

Figure 9:
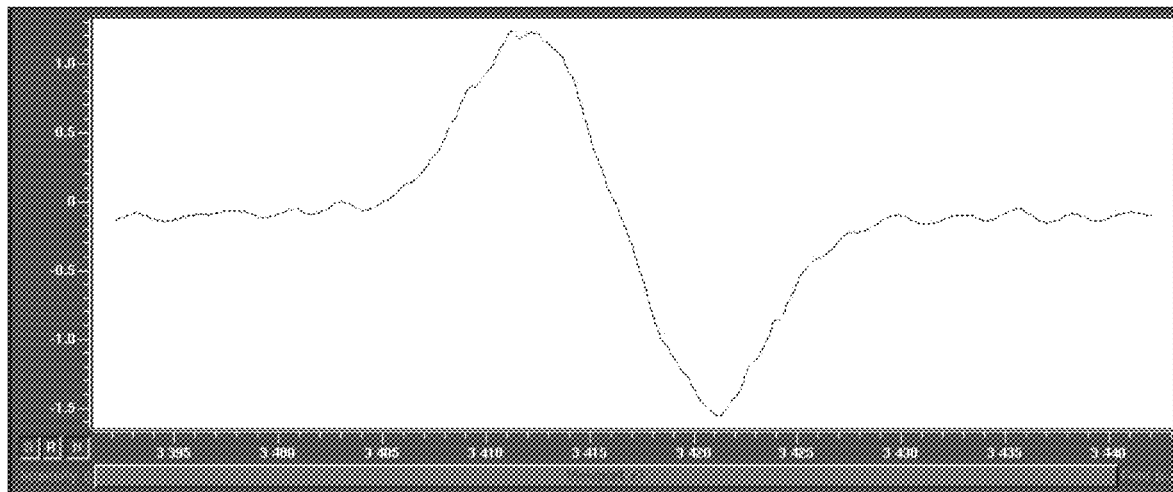
FIG. 9 shows an EPR spectrum wherein P1 and P2 Centers are located.

In order to quantify the N3 and C-center content in diamond, a spectrum focused in P2 and P1 center is collected under higher power and modulation amplitude. The resulting spectrum of which is shown in FIG. 9 whereby there is shown an EPR spectrum wherein P1 and P2 Centers are located, which is focused in the selected range and will be later used for spin counting.

Figure 10:
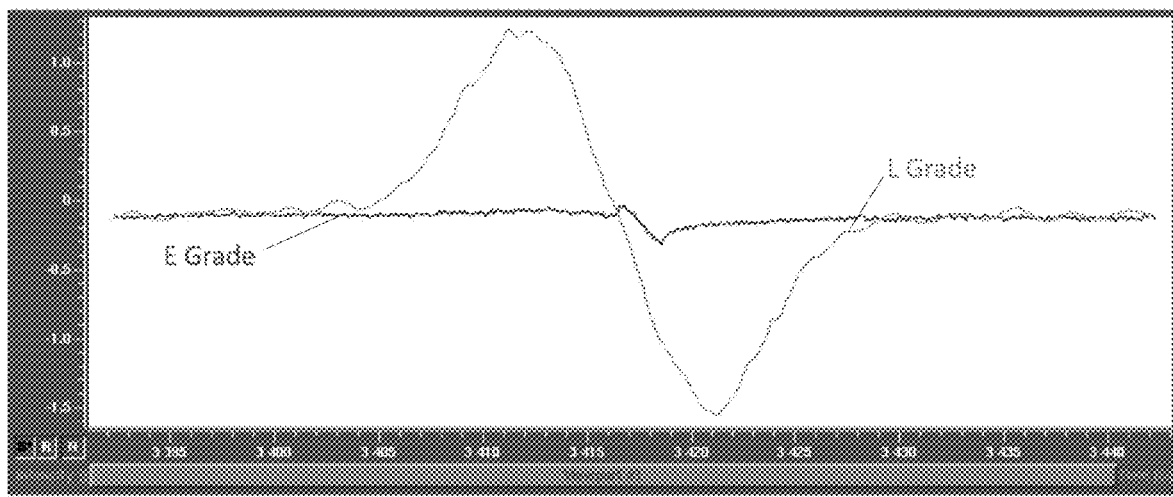
FIG. 10 shows an EPR spectrum of grade E and grade L diamonds of the master stone set, wherein the difference in signal density between the two is presented.

As is shown in FIG. 10, an observable difference in the signal intensity between different colour grades is shown and demonstrated in FIG. 10, whereby the EPR spectrum of E and L grade diamond is provided showing the difference in signal intensity.

As is demonstrated from the measurements above at FIGS. 8 and 10, the difference in signal intensity between colour grades is distinct and clearly observable.

The signal clearly increases upon movement further along the grade scale. The quantification of P2 and P1 center (N3+C-center) will be processed through spin counting.

Figure 11:
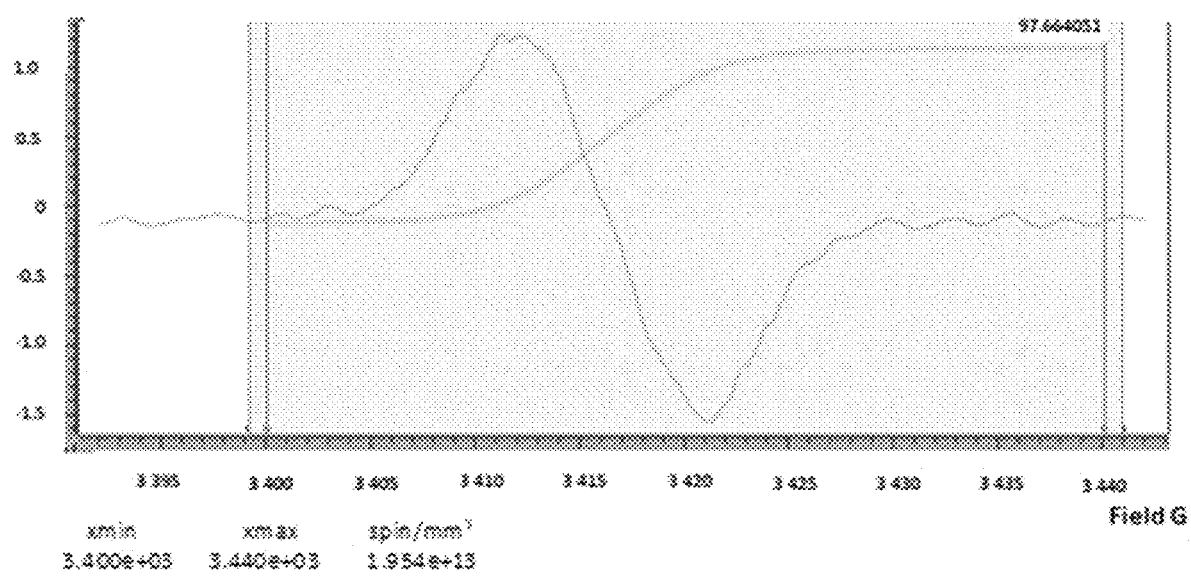
FIG. 11 shows a range selection of the spectrum for spin counting of the P1 and P2 Centers.

Spin counting, an intrinsic quantitative function in Bruker, was conducted after obtaining a spectrum centered where P2 and P1 center were located, as is shown in FIG. 11.

For the spin counting calculation, it is necessary to obtain the value of the inner diameter of the tube utilised, as well as, the height of the sample inside the tube, prior to the performance of the calculation.

As diamonds can be considered somewhat irregular in shape, the actual height that is occupied in the tube by the diamond is calculated from its volume using the formula below:

$$\text{Volume (mm}^3\text{)} = \pi r^2 h,$$

where r is the inner radius of the EPR tube and h the height of the tube that the sample occupies.

The volume of the diamond sample can be converted based on its weight in grams or carats. The total spin (spins/mm$^3$) shown after Spin Counting is the number of spins that is present per volume (per mm$^3$) in the sample.

To calculate the Total P2+P1 center spins in the sample diamond used, the following is used:

$$\text{Total } P2+P1 \text{ center spins} = N/n° \text{ of } C \text{ atoms in the sample,}$$

Where $N = S*V$, with S being the number of spins/mm$^3$ given by Spin Counting and V being the volume of the sample.

Figure 12:
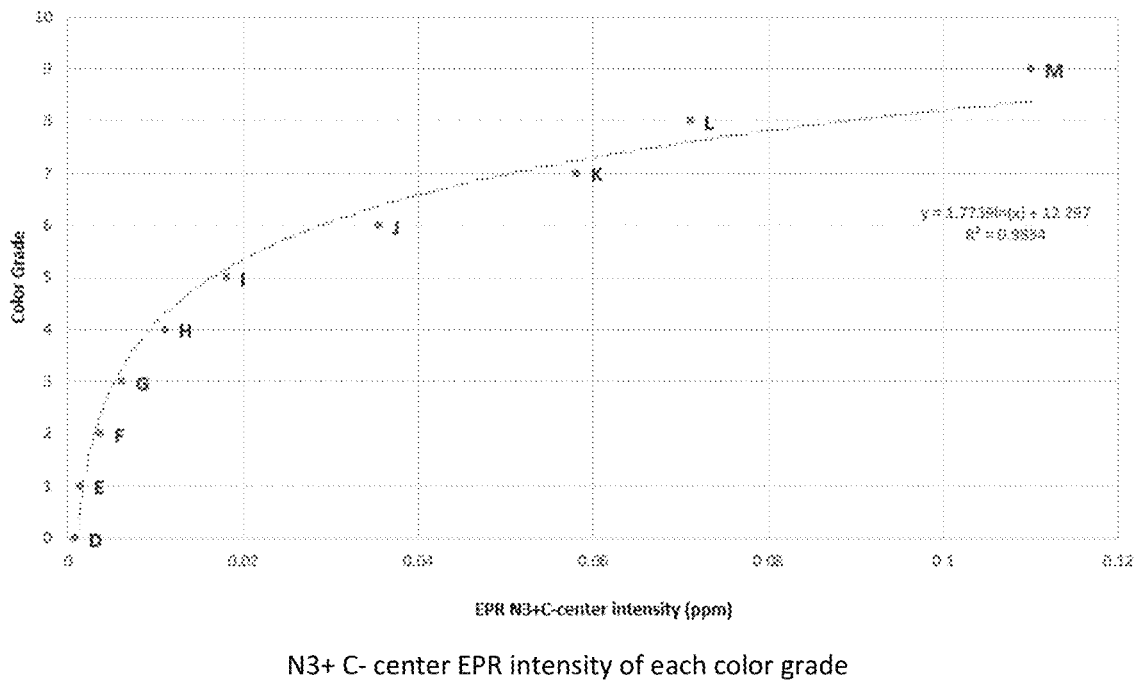
FIG. 12 schematically depicts the N3+C-center EPR intensity of each colour grade of the master stone set.

The intensity of N3+C-center (ppm) is normalized against their respective carat weight and shown in FIG. 12.

Table 2 as shown below summarises the total number of spins of N3+C-center in ppm.

TABLE 3

N3 + C-center EPR intensity of each colour grade.

| Master Colour Set | | N3 + C-center intensity (ppm) |
|---|---|---|
| 0 | D | 0.0008047 |
| 1 | E | 0.0013584 |
| 2 | F | 0.0036994 |
| 3 | G | 0.0061923 |
| 4 | H | 0.0111028 |
| 5 | I | 0.0180881 |
| 6 | J | 0.0355232 |
| 7 | K | 0.0581547 |

TABLE 3-continued

N3 + C-center EPR intensity of each colour grade.

| Master Colour Set | | N3 + C-center intensity (ppm) |
|---|---|---|
| 8 | L | 0.0711033 |
| 9 | M | 0.1100624 |

As is demonstrated, the intensity of N3+C-center in a diamond increases exponentially as its grade increases on the Colour Grade scale.

Figure 13:
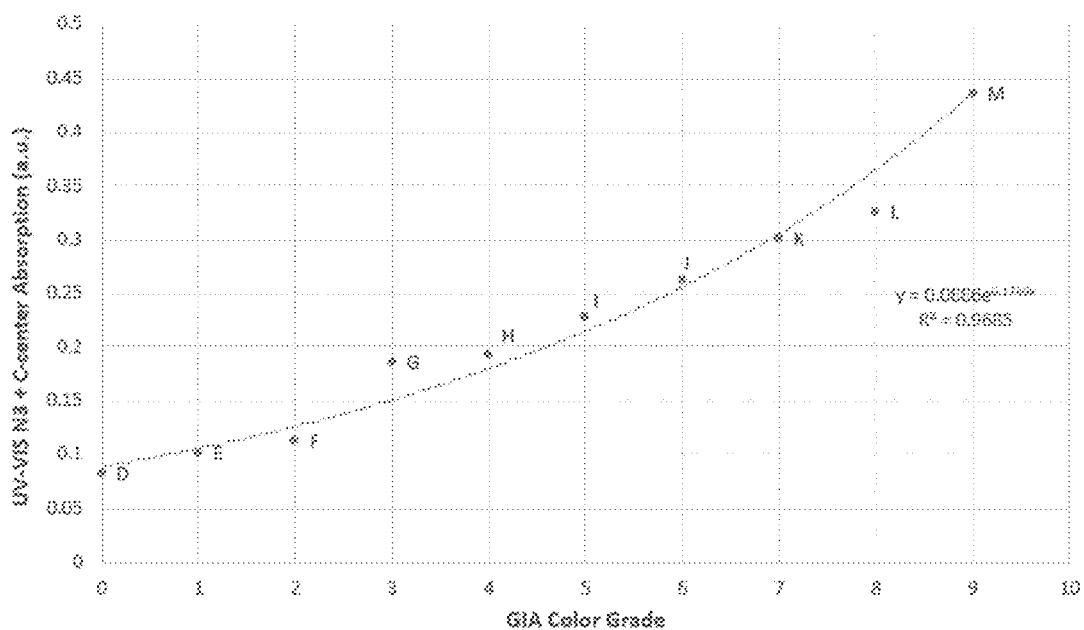
FIG. 13 schematically depicts the UV-Vis N3+C-center absorbance concentration of each colour grade diamond of the master stone set.

Further, an increasing trend can be seen also in the UV-Vis absorption data as shown in reference to FIG. 13.

Table 4 below summaries the total number of UV-VIS absorption signal of N3+C-center in ppm.

TABLE 4

N3 + C-center UV-Vis absorption intensity of each colour grade.

| Master Colour Set | | N3 + C-center absorption (a.u.) |
|---|---|---|
| 0 | D | 0.083 |
| 1 | E | 0.101 |
| 2 | F | 0.113 |
| 3 | G | 0.186 |
| 4 | H | 0.192 |
| 5 | I | 0.228 |
| 6 | J | 0.262 |
| 7 | K | 0.301 |
| 8 | L | 0.325 |
| 9 | M | 0.435 |

However, it is noted that variations are present within the trend, especially in reference to FIG. 13 for D to G grade diamonds, and it is considered that this may be influenced in relation to a relatively small sample size of the colour set used.

The reference colour set as utilised is comprised mainly of diamonds that fall in the high and middle colour range. Despite the fact that there is some degree of variation, it is clearly shown that the N3 center and C-center are very strongly correlated with colour grades, suggesting and supporting that the higher the concentration of both centers, the lower the grade of colour of a diamond.

Figure 14:
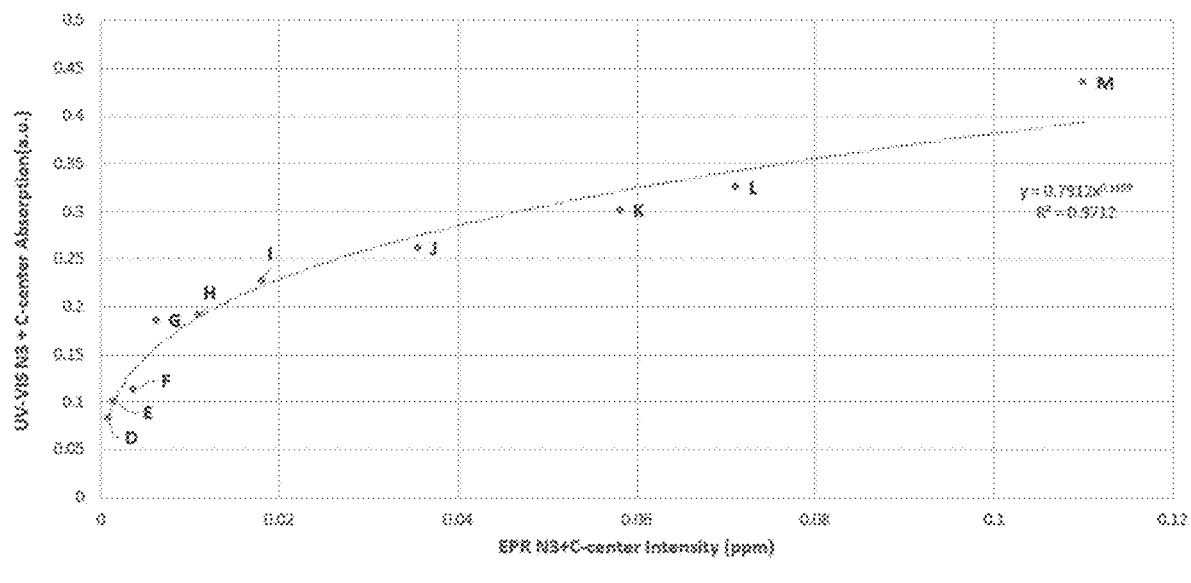
FIG. 14 schematically depicts the correlation between N3+C-center intensity obtained in UV-Vis and EPR.
Figure 15:
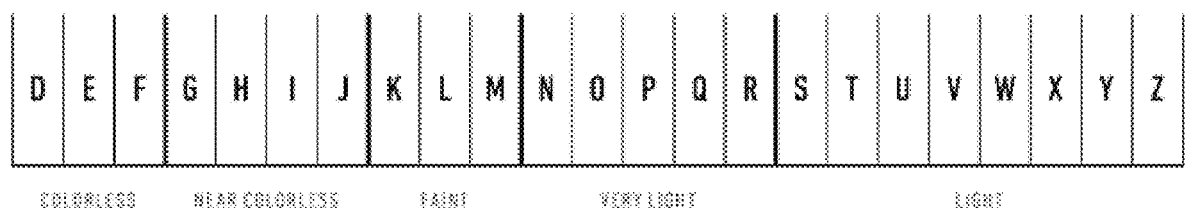
FIG. 15 is an illustration of the Gemological Institute of America (GIA) colour scale, against which a colour grading is applied, with the grades from colourless to light.

For further analysis, the present inventors have plotted UV-Vis absorbance results against EPR concentration results, which can be considered a much more independent variable compared to colour grades such as GIA colour grades. As is shown in FIG. 14, there is indicated a power function with a fairly high correlation. Furthermore, it is noted that this result does not face the variables that optical-based instruments encounters such as light path, the distance from the sample, the area covered and the like.

Rather, EPR results are calculated from the number of electron spins of paramagnetic defects (N3 and C-center) present in the whole diamond sample offering an independent and self-consistent quantitative result, and whereby as discussed above N3 and C-center are considered to be the main contributors of optically observable yellowness, which pertains directly to colour.

Importantly, the data set as derived and as shown in FIG. 14, can be used as "Standard" data set for a standard for the grading of the colour of a diamond, as described and claimed in the present invention.

By building a standard reference data set for colour grading, based on an acceptable and appropriate original set of master stones, obviates the necessity of multiple master stone sets and provides a standard reference point using repeatable data based on inherent aspects of a diamond, and thus obviates subjectivity.

Further, as such a standard reference data set for colour can be built based on a master set of stones for which consensus has been given as to their applicability for colour grading, the resultant grading is immediately commercially relevant.

Still further, such a data set is based on normalized quantifiable data and as such, can be used for consistent colour grading for stones of different size.

5.5 Concluding Comments on of Experimental Evaluation and Model

In accordance with the present invention, it has been shown that EPR and UV-Vis Spectroscopy is successful in revealing the relationship between N3 center and C-center concentration and the colour grade scale by showing a strong correlation.

It has been observed that upon advancement of diamonds on a colour grade scale, the N3+C-center concentration increases.

The invention demonstrates that EPR is able to provide accurately an actual figure of N3 and C-center concentration based solely on the number of spins present in the sample, a quantitative method that cannot be achieved with optical based instruments.

Thus, it is certain and has been demonstrated that EPR can be used as tool in the measurement and quantification of diamond paramagnetic defects, and can be used for determination of the colour of a diamond according to the present invention.

6. REFERENCES

1. King, J. M., et al., *COLOUR GRADING "D-TO-Z"DIAMONDS AT THE GIA LABORATORY.* GEMS&GEMOLOGY, Winter 2008: p. 296-321.
2. Babamoradi, M., et al., *Many-electron states of the N2 and N3 colour centers in diamond: A first-principles and many-body study.* Physica B: Condensed Matter, 2017. 505: p. 17-21.
3. Collins, A. T., *The detection of colour-enhanced and synthetic gem diamonds by optical spectroscopy.* Diamond and Related Materials, 2003. 12 (10): p. 1976-1983.
4. Inga A. Dobrinets, et al., *HPHT-Treated Diamonds.* Springer, 2013. 181: p. 188.
5. Hall, L. T., et al., *Detection of nanoscale electron spin resonance spectra demonstrated using nitrogen-vacancy centre probes in diamond.* Nat Commun, 2016. 7: p. 1-9.
6. Nadolinny, V., A. Komarovskikh, and Y. Palyanov, *Incorporation of Large Impurity Atoms into the Diamond Crystal Lattice: EPR of Split-Vacancy Defects in Diamond.* Crystals, 2017. v2: p. 237.
7. Wyk, J. A. v., *Carbon-12 hyperfine interaction of the unique carbon of the P2 (ESR) or N3 (optical) centre in diamond.* J. Phys. C: Solid State Phys. 15 L981, 1982. 15.
8. Nadolinny, V., et al., *The influence of HTHP treatment on the OK1 and N3 centers in natural diamond crystals.* physica status solidi (a), 2015. 212 (11): p. 2474-2479.
9. Laraoui, A., J. S. Hodges, and C. A. Meriles, *Nitrogen-Vacancy-Assisted Magnetometry of Paramagnetic Centers in an Individual Diamond Nanocrystal.* Nano Letters, 2012. 12 (7): p. 3477-3482.
10. Bruker. *EPR in industry.* https://www.bruker.com/products/mr/epr/epr-in-industry.html.

The invention claimed is:

1. A process of assigning a colour grade to a diamond, said process including the steps of:
   (i) determining the N3 and C-center content of a diamond;
   (ii) comparing the N3 and C-center content of said diamond with a previously acquired data set from a plurality of diamonds each having a colour grading previously assigned thereto, and
   (iii) assigning a colour grade to the diamond upon a correlation of the N3 and C-center content of said diamond with a grade of said previously acquired data set;
   wherein said previously acquired data set comprises a correlation between N3 and C center content and optical absorbance in the visible light spectrum for each diamond of said plurality of diamonds.

2. The process according to claim 1, wherein the N3 and C-center content of the diamond is determined by Electron paramagnetic resonance (EPR).

3. The process according to claim 1, wherein said optical absorbance is N3 and C-center absorbance in the Ultraviolet Visible (UV-Vis) spectrum.

4. The process according to claim 3, wherein said N3 and C-center absorbance is determined by way of a UV-Vis-NIR Spectrometer.

5. A process of assigning a colour grade to a diamond, said process including the steps of:
   (i) determining the optical absorbance in the visible light spectrum of a diamond;
   (ii) comparing the optical absorbance of said diamond with previously acquired data set from a plurality of diamonds each having a colour grading previously assigned thereto, and
   (iii) assigning a colour grade to the diamond upon a correlation of the optical absorbance of said diamond with a grade of said previously acquired data set;
   wherein said previously acquired data set comprises a correlation between N3 and C center content and optical absorbance in the visible light spectrum for each diamond of said plurality of diamonds.

6. The process according to claim 5, wherein the N3 and C-center content of the diamond is determined by Electron paramagnetic resonance (EPR).

7. The process according to claim 5, wherein said optical absorbance is N3 and C-center absorbance in the Ultraviolet Visible (UV-Vis) spectrum.

8. The process according to claim 7, wherein said N3 and C-center absorbance is determined by way of a UV-Vis-NIR Spectrometer.

* * * * *